United States Patent
Ueno

(10) Patent No.: US 8,114,911 B2
(45) Date of Patent: Feb. 14, 2012

(54) PROSTAGLANDIN COMPOUNDS FOR THE TREATMENT OF OBESITY

(75) Inventor: Ryuji Ueno, Montgomery, MD (US)

(73) Assignee: Sucampo AG, Zug (CH)

( * ) Notice: Subject to any disclaimer, the term of this patent is extended or adjusted under 35 U.S.C. 154(b) by 404 days.

(21) Appl. No.: 10/531,874

(22) PCT Filed: Oct. 22, 2003

(86) PCT No.: PCT/JP03/13453
§ 371 (c)(1), (2), (4) Date: Apr. 19, 2005

(87) PCT Pub. No.: WO2004/037268
PCT Pub. Date: May 6, 2004

(65) Prior Publication Data
US 2005/0261373 A1    Nov. 24, 2005

(51) Int. Cl.
*A61K 31/557* (2006.01)
(52) U.S. Cl. ........................ 514/573; 514/909
(58) Field of Classification Search .................... None
See application file for complete search history.

(56) References Cited

U.S. PATENT DOCUMENTS

| | | | |
|---|---|---|---|
| 3,888,919 A * | 6/1975 | Pike et al. ................. | 562/503 |
| 5,073,569 A | 12/1991 | Ueno et al. | |
| 5,166,174 A | 11/1992 | Ueno et al. | |
| 5,212,324 A | 5/1993 | Ueno | |
| 5,221,763 A | 6/1993 | Ueno et al. | |
| 5,234,954 A * | 8/1993 | Ueno et al. | |
| 5,284,858 A | 2/1994 | Ueno et al. | |
| 5,317,032 A | 5/1994 | Ueno et al. | |
| 5,739,161 A | 4/1998 | Ueno | |
| 6,242,485 B1 | 6/2001 | Ueno | |
| 6,414,016 B1 | 7/2002 | Ueno | |
| 6,583,174 B1 | 6/2003 | Ueno et al. | |
| 6,830,882 B1 * | 12/2004 | Evans et al. ................. | 435/6 |
| 6,956,056 B2 | 10/2005 | Ueno | |
| 6,982,283 B2 | 1/2006 | Ueno | |
| 7,064,148 B2 | 6/2006 | Ueno et al. | |
| 2003/0119898 A1 | 6/2003 | Ueno et al. | |
| 2003/0166632 A1 | 9/2003 | Ueno | |
| 2004/0138308 A1 | 7/2004 | Ueno et al. | |
| 2004/0235885 A1 | 11/2004 | Ueno et al. | |
| 2005/0222195 A1 | 10/2005 | Ueno | |
| 2005/0261375 A1 | 11/2005 | Ueno | |
| 2006/0063830 A1 | 3/2006 | Ueno | |
| 2006/0240106 A1 | 10/2006 | Ueno | |
| 2006/0281818 A1 | 12/2006 | Ueno et al. | |
| 2007/0276006 A1 | 11/2007 | Ueno | |

FOREIGN PATENT DOCUMENTS

| | | |
|---|---|---|
| EP | 410646 | 1/1991 |
| JP | 2000-157260 A | 6/2000 |
| NZ | 228111 | 2/1991 |
| NZ | 226198 | 5/1991 |
| NZ | 226199 | 5/1991 |
| WO | WO 96/33724 A | 10/1996 |
| WO | WO 99/53927 A | 10/1999 |

OTHER PUBLICATIONS

Dietz, W., "Health Consequences of Obesity in Youth: Childhood Predictors of Adult Disease", Mar. 1998, vol. 101, Issue 3 Supplement, pp. 518-525.*
The Merck Manual, "Obesity: Disorders of Nutrition and Metabolism", Merck Manual of Medical Information—Second Home Edition, 2003, downloaded from "http://www.merck.com/mmhe/print/sec12/ch156a.html", pp. 1-8 of 8.*
Edith Polis and Freeman W. Cope; Dose-Dependent Reduction of Hereditary Obesity in the Non-Diabetic Mouse by Polymeric Prostglandin $PGB_x$; Physiological Chemistry and Physics, United States, 1980, vol. 12, No. 6, pp. 564-568.

* cited by examiner

*Primary Examiner* — James D Anderson
*Assistant Examiner* — Gregg Polansky
(74) *Attorney, Agent, or Firm* — Sughrue Mion, PLLC

(57) ABSTRACT

Provided is a composition for treating obesity which comprises an effective amount of a prostaglandin compound, especially, a compound of formula (I).

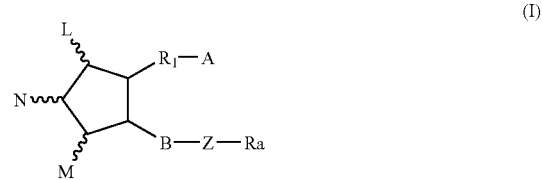

(I)

12 Claims, 1 Drawing Sheet

PROSTAGLANDIN COMPOUNDS FOR THE TREATMENT OF OBESITY

CROSS REFERENCE TO RELATED APPLICATIONS

This application is the National Stage of PCT/JP03/13453 filed Oct. 22, 2003, which claims benefit of Provisional Application No. 60/420,336 filed Oct. 23, 2002.

TECHNICAL FIELD

The present invention relates to a method and composition for treating obesity.

BACKGROUND ART

Obesity, according to its cause, is classified into two groups, i.e. primary obesity (simple obesity) and secondary obesity (symptomatic obesity). The cause of primary obesity includes excessive energy intake, insufficient energy consumption and decreased thermogenesis. Today, primary obesity accounts for a large majority of diagnosed cases of obesity. Development and persistent of primary obesity may cause various health problems.

The secondary obesity is caused by certain underlying disorders and is also diagnosed as obesity. Examples of secondary obesity include endocrine obesity, hypothalamic obesity, hereditary obesity and drug-induced obesity.

Obesity is a risk factor for health. It may induce strain on the circulatory system, metabolic disorders such as diabetes, liver- or biliary-system disorders, respiratory depression as well as excessive weight on the bones and the joints.

Therapeutic approaches used for treating obesity include alimentotherapy, ergotherapy, behavioral therapy, psychotherapy and drug therapy. The alimentotherapy reduces the body weight by reducing total calorie intake with controlled diet. The method, however, often results in a lowered resting metabolic rate, which makes it harder to keep the weight off once the patient attained. Ergotherapy not only increases energy consumption, but also increases the resting metabolic rate and normalize the insulin resistance, and can effectively decrease the body fat. The big problem of the ergotherapy is the difficulty in carrying out the therapy continuously over a long period of time. The behavioral therapy and psychotherapy are carried out to support the alimentotherapy and/or ergotherapy, but they hardly bring sufficient effects.

Examples of the obesity drugs used for the drug therapy include appetite suppressant such as mazindol, fenfluramine, fluoxetine and cholecystokinin, agents to reduce digestive absorption such as acarbose, voglibose and lipostatin, agents to inhibit fat accumulation such as nafenopin, hydroxy oxalic acid and imidazole acetophen, and metabolic accelerators such as β3 receptor stimulant. However, such conventional obesity drugs may cause adverse side effects such as drug dependence, and patients having received such drugs may become resistant to the drugs in a short period. Accordingly, the conventionally used obesity drugs are not suitable for long term continuous treatment.

It has been desired in the art to develop an effective anti-obesity drug without or with decreased side effects, that can be continuously used for a long period without imposing burden on patients.

Prostaglandins (hereinafter, referred to as PG(s)) are members of class of organic carboxylic acids, which are contained in tissues or organs of human or other mammals, and exhibit a wide range of physiological activity. PGs found in nature (primary PGs) generally have a prostanoic acid skeleton as shown in the formula (A):

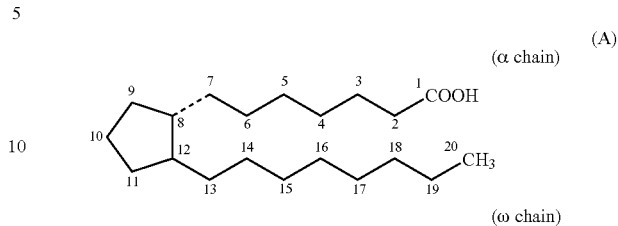

On the other hand, some of synthetic analogues of primary PGs have modified skeletons. The primary PGs are classified to PGAs, PGBs, PGCs, PGDs, PGEs, PGFs, PGGs, PGHs, PGIs and PGJs according to the structure of the five-membered ring moiety, and further classified into the following three types by the number and position of the unsaturated bond at the carbon chain moiety:
Subscript 1: 13,14-unsaturated-15-OH
Subscript 2: 5,6- and 13,14-diunsaturated-15-OH
Subscript 3: 5,6-, 13,14-, and 17,18-triunsaturated-15-OH.

Further, the PGFs are classified, according to the configuration of the hydroxyl group at the 9-position, into α type (the hydroxyl group is of an α-configuration) and β type (the hydroxyl group is of a β-configuration).

$PGE_1$ and $PGE_2$ and $PGE_3$ are known to have vasodilation, hypotension, gastric secretion decreasing, intestinal tract movement enhancement, uterine contraction, diuretic, bronchodilation and anti ulcer activities. $PGF_{1\alpha}$, $PGF_{2\alpha}$ and $PGF_{3\alpha}$ have been known to have hypertension, vasoconstriction, intestinal tract movement enhancement, uterine contraction, lutein body atrophy and bronchoconstriction activities.

However, it is not known how prostaglandin compounds act on obesity.

SUMMARY OF THE INVENTION

The present invention relates to a method for treating obesity in a mammalian subject, which comprises administration of an effective amount of a prostaglandin compound to the subject in need of such treatment.

The present invention further relates to a pharmaceutical composition for treating obesity in a mammalian subject, which comprises an effective amount of a prostaglandin compound.

Further more, the present invention relates to use of a prostaglandin compound for manufacturing a pharmaceutical composition for treating obesity in a mammalian subject.

DETAILED DESCRIPTION OF THE INVENTION

Figure 1:
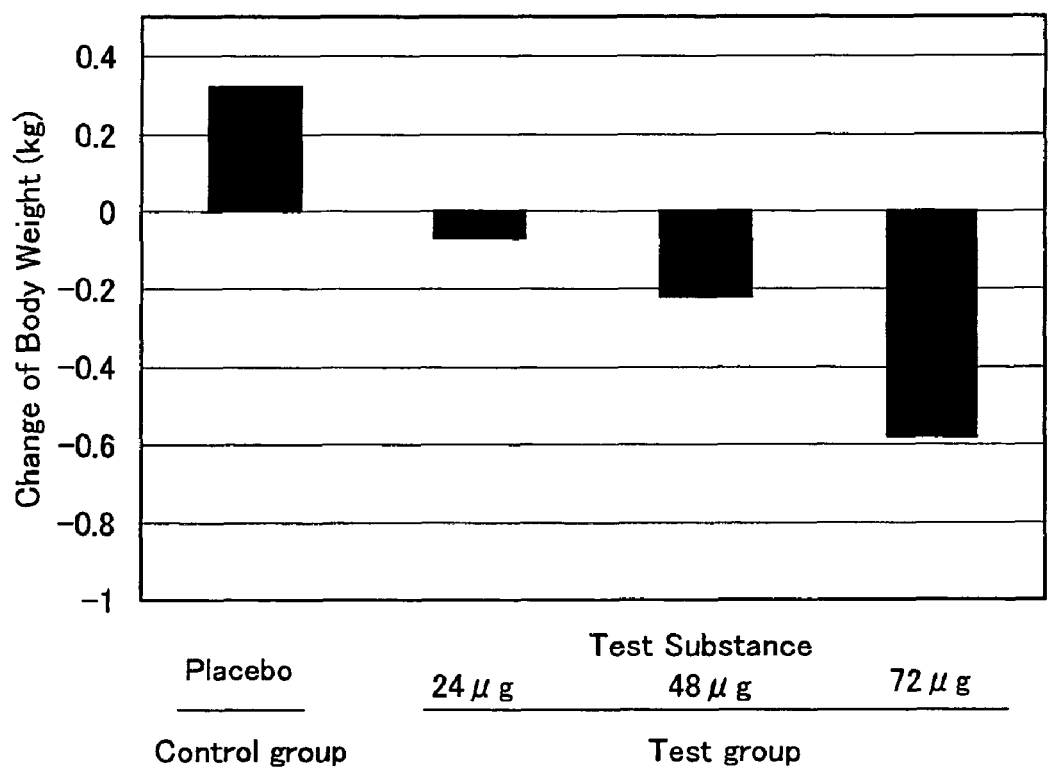
FIG. 1 represents result of the example.

The nomenclature of the PG compounds used herein is based on the numbering system of the prostanoic acid represented in the above formula (A).

The formula (A) shows a basic skeleton of the C-20 carbon atoms, but the present invention is not limited to those having the same number of carbon atoms. In the formula (A), the numbering of the carbon atoms which constitute the basic skeleton of the PG compounds starts at the carboxylic acid (numbered 1), and carbon atoms in the α-chain are numbered 2 to 7 towards the five-membered ring, those in the ring are 8 to 12, and those in the ω-chain are 13 to 20. When the number of carbon atoms is decreased in the α-chain, the number is deleted in the order starting from position 2; and when the number of carbon atoms is increased in the α-chain, compounds are named as substitution compounds having respective substituents at position 2 in place of the carboxy group (C-1). Similarly, when the number of carbon atoms is decreased in the α-chain, the number is deleted in the order starting from position 20; and when the number of carbon atoms is increased in the ω-chain, the carbon atoms beyond position 20 are named as substituents. Stereochemistry of the compounds is the same as that of the above formula (A) unless otherwise specified.

In general, each of the terms PGD, PGE and PGF represents a PG compound having hydroxy groups at positions 9 and/or 11, but in the present specification, these terms also include those having substituents other than the hydroxy group at positions 9 and/or 11. Such compounds are referred to as 9-dehydroxy-9-substituted-PG compounds or 11-dehydroxy-11-substituted-PG compounds. A PG compound having hydrogen in place of the hydroxy group is simply named as 9- or 11-dehydroxy-PG compound.

As stated above, the nomenclature of the PG compounds is based on the prostanoic acid skeleton. However, in case the compound has a similar partial structure as a prostaglandin, the abbreviation of "PG" may be used. Thus, a PG compound of which α-chain is extended by two carbon atoms, that is, having 9 carbon atoms in the α-chain is named as 2-decarboxy-2-(2-carboxyethyl)-PG compound. Similarly, a PG compound having 11 carbon atoms in the α-chain is named as 2-decarboxy-2-(4-carboxybutyl)-PG compound. Further, a PG compound of which ω-chain is extended by two carbon atoms, that is, having 10 carbon atoms in the ω-chain is named as 20-ethyl-PG compound. These compounds, however, may also be named according to the IUPAC nomenclatures.

Examples of the analogs (including substituted derivatives) or derivatives include a PG compound of which carboxy group at the end of α-chain is esterified; a compound of which α-chain is extended; physiologically acceptable salt thereof; a compound having a double bond at 2-3 position or a triple bond at position 5-6, a compound having substituent(s) at position 3, 5, 6, 16, 17, 18, 19 and/or 20; and a compound having lower alkyl or a hydroxy (lower)alkyl group at position 9 and/or 11 in place of the hydroxy group.

According to the present invention, preferred substituents at position 3, 17, 18 and/or 19 include alkyl having 1-4 carbon atoms, especially methyl and ethyl. Preferred substituents at position 16 include lower alkyl such as methyl and ethyl, hydroxy, halogen atoms such as chlorine and fluorine, and aryloxy such as trifluoromethylphenoxy. Preferred substituents at position 17 include lower alkyl such as methyl and ethyl, hydroxy, halogen atoms such as chlorine and fluorine, aryloxy such as trifluoromethylphenoxy. Preferred substituents at position 20 include saturated or unsaturated lower alkyl such as C1-4 alkyl, lower alkoxy such as C1-4 alkoxy, and lower alkoxy alkyl such as C1-4 alkoxy-C1-4 alkyl. Preferred substuents at position 5 include halogen atoms such as chlorine and fluorine. Preferred substituents at position 6 include an oxo group forming a carbonyl group. Stereochemistry of PGs having hydroxy, lower alkyl or hydroxy(lower) alkyl substituent at position 9 and/or 11 may be α, β or a mixture thereof.

Further, the above analogs or derivatives may be compounds having an alkoxy, cycloalkyl, cycloalkyloxy, phenoxy or phenyl group at the end of the ω-chain where the chain is shorter than the primary PGs.

A preferred compounds used in the present invention is represented by the formula (I):

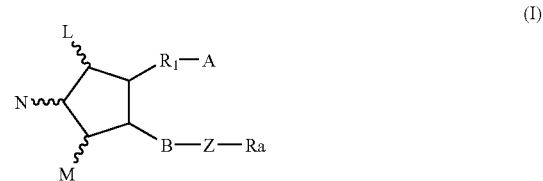

wherein L, M and N are hydrogen, hydroxy, halogen, lower alkyl, hydroxy(lower)alkyl, lower alkanoyloxy or oxo, wherein at least one of L and M is a group other than hydrogen, and the five-membered ring may have at least one double bond;

A is —CH₃, or —CH₂OH, —COCH₂OH, —COOH or a functional derivative thereof;

B is single bond, —CH₂—CH₂—, —CH=CH—, —C≡C—, —CH₂—CH₂—CH₂—, —CH=CH—CH₂—, —CH₂—CH=CH—, —C≡C—CH₂— or —CH₂—C≡C—;

Z is

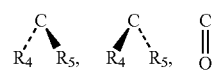

or single bond wherein R₄ and R₅ are hydrogen, hydroxy, halogen, lower alkyl, lower alkoxy or hydroxy(lower)alkyl, wherein R₄ and R₅ are not hydroxy and lower alkoxy at the same time;

R₁ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and Ra is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

A preferred compounds used in the present invention is represented by the formula (II):

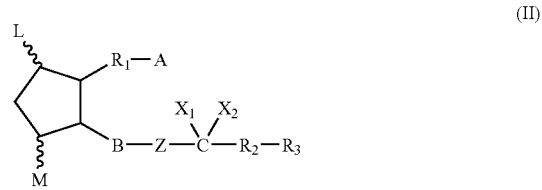

wherein L and M are hydrogen, hydroxy, halogen, lower alkyl, hydroxy(lower)alkyl, lower alkanoyloxy or oxo, wherein at least one of L and M is a group other than hydrogen, and the five-membered ring may have one or more double bonds;

A is —CH₃, or —CH₂OH, —COCH₂OH, —COOH or a functional derivative thereof;

B is single bond, —CH₂—CH₂—, —CH=CH—, —C≡C—, —CH₂—CH₂—CH₂—, —CH=CH—CH₂—, —CH₂—CH=CH—, —C≡C—CH₂— or —CH₂—C≡C—;

Z is

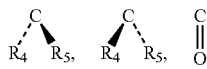

or single bond wherein $R_4$ and $R_5$ are hydrogen, hydroxy, halogen, lower alkyl, lower alkoxy or hydroxy(lower)alkyl, wherein $R_4$ and $R_5$ are not hydroxy and lower alkoxy at the same time;

$X_1$ and $X_2$ are hydrogen, lower alkyl, or halogen;

$R_1$ is a saturated or unsaturated bivalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur;

$R_2$ is a single bond or lower alkylene; and $R_3$ is lower alkyl, lower alkoxy, lower alkanoyloxy, cyclo (lower)alkyl, cyclo(lower)alkyloxy, aryl, aryloxy, heterocyclic group or heterocyclic-oxy group.

In the above formula, the term "unsaturated" in the definitions for $R_1$ and Ra is intended to include at least one or more double bonds and/or triple bonds that are isolatedly, separately or serially present between carbon atoms of the main and/or side chains. According to the usual nomenclature, an unsaturated bond between two serial positions is represented by denoting the lower number of the two positions, and an unsaturated bond between two distal positions is represented by denoting both of the positions.

The term "lower or medium aliphatic hydrocarbon" refers to a straight or branched chain hydrocarbon group having 1 to 14 carbon atoms (for a side chain, 1 to 3 carbon atoms are preferable) and preferably 1 to 10, especially 1 to 8 carbon atoms.

The term "halogen atom" covers fluorine, chlorine, bromine and iodine.

The term "lower" throughout the specification is intended to include a group having 1 to 6 carbon atoms unless otherwise specified.

The term "lower alkyl" refers to a straight or branched chain saturated hydrocarbon group containing 1 to 6 carbon atoms and includes, for example, methyl, ethyl, propyl, isopropyl, butyl, isobutyl, t-butyl, pentyl and hexyl.

The term "lower alkylene" refers to a straight or branched chain bivalent saturated hydrocarbon group containing 1 to 6 carbon atoms and includes, for example, methylene, ethylene, propylene, isopropylene, butylene, isobutylene, t-butylene, pentylene and hexylene.

The term "lower alkoxy" refers to a group of lower alkyl-O—, wherein lower alkyl is as defined above.

The term "hydroxy(lower)alkyl" refers to a lower alkyl as defined above which is substituted with at least one hydroxy group such as hydroxymethyl, 1-hydroxyethyl, 2-hydroxyethyl and 1-methyl-1-hydroxyethyl. The term "lower alkanoyloxy" refers to a group represented by the formula RCO—O—, wherein RCO— is an acyl group formed by oxidation of a lower alkyl group as defined above, such as acetyl.

The term "cyclo(lower)alkyl" refers to a cyclic group formed by cyclization of a lower alkyl group as defined above but contains three or more carbon atoms, and includes, for example, cyclopropyl, cyclobutyl, cyclopentyl and cyclohexyl.

The term "cyclo(lower)alkyloxy" refers to the group of cyclo(lower)alkyl-O—, wherein cyclo(lower)alkyl is as defined above.

The term "aryl" may include unsubstituted or substituted aromatic hydrocarbon rings (preferably monocyclic groups), for example, phenyl, tolyl, xylyl. Examples of the substituents are halogen atom and halo(lower)alkyl, wherein halogen atom and lower alkyl are as defined above.

The term "aryloxy" refers to a group represented by the formula ArO—, wherein Ar is aryl as defined above.

The term "heterocyclic group" may include mono- to tricyclic, preferably monocyclic heterocyclic group which is 5 to 14, preferably 5 to 10 membered ring having optionally substituted carbon atom and 1 to 4, preferably 1 to 3 of 1 or 2 type of hetero atoms selected from nitrogen atom, oxygen atom and sulfur atom. Examples of the heterocyclic group include furyl, thienyl, pyrrolyl, oxazolyl, isoxazolyl, thiazolyl, isothiazolyl, imidazolyl, pyrazolyl, furazanyl, pyranyl, pyridyl, pyridazinyl, pyrimidyl, pyrazinyl, 2-pyrrolinyl, pyrrolidinyl, 2-imidazolinyl, imidazolidinyl, 2-pyrazolinyl, pyrazolidinyl, piperidino, piperazinyl, morpholino, indolyl, benzothienyl, quinolyl, isoquinolyl, purinyl, quinazolinyl, carbazolyl, acridinyl, phenanthridinyl, benzimidazolyl, benzimidazolinyl, benzothiazolyl, phenothiazinyl. Examples of the substituent in this case include halogen, and halogen substituted lower alkyl group, wherein halogen atom and lower alkyl group are as described above.

The term "heterocyclic-oxy group" means a group represented by the formula HcO—, wherein Hc is a heterocyclic group as described above.

The term "functional derivative" of A includes salts (preferably pharmaceutically acceptable salts), ethers, esters and amides.

Suitable "pharmaceutically acceptable salts" include conventionally used non-toxic salts, for example a salt with an inorganic base such as an alkali metal salt (such as sodium salt and potassium salt), an alkaline earth metal salt (such as calcium salt and magnesium salt), an ammonium salt; or a salt with an organic base, for example, an amine salt (such as methylamine salt, dimethylamine salt, cyclohexylamine salt, benzylamine salt, piperidine salt, ethylenediamine salt, ethanolamine salt, diethanolamine salt, triethanolamine salt, tris (hydroxymethylamino)ethane salt, monomethyl-monoethanolamine salt, procaine salt and caffeine salt), a basic amino acid salt (such as arginine salt and lysine salt), tetraalkyl ammonium salt and the like. These salts may be prepared by a conventional process, for example from the corresponding acid and base or by salt interchange.

Examples of the ethers include alkyl ethers, for example, lower alkyl ethers such as methyl ether, ethyl ether, propyl ether, isopropyl ether, butyl ether, isobutyl ether, t-butyl ether, pentyl ether and 1-cyclopropyl ethyl ether; and medium or higher alkyl ethers such as octyl ether, diethylhexyl ether, lauryl ether and cetyl ether; unsaturated ethers such as oleyl ether and linolenyl ether; lower alkenyl ethers such as vinyl ether, allyl ether; lower alkynyl ethers such as ethynyl ether and propynyl ether; hydroxy(lower)alkyl ethers such as hydroxyethyl ether and hydroxyisopropyl ether; lower alkoxy (lower)alkyl ethers such as methoxymethyl ether and 1-methoxyethyl ether; optionally substituted aryl ethers such as phenyl ether, tosyl ether, t-butylphenyl ether, salicyl ether, 3,4-di-methoxyphenyl ether and benzamidophenyl ether; and aryl(lower)alkyl ethers such as benzyl ether, trityl ether and benzhydryl ether.

Examples of the esters include aliphatic esters, for example, lower alkyl esters such as methyl ester, ethyl ester, propyl ester, isopropyl ester, butyl ester, isobutyl ester, t-butyl ester, pentyl ester and 1-cyclopropylethyl ester; lower alkenyl esters such as vinyl ester and allyl ester; lower alkynyl esters such as ethynyl ester and propynyl ester; hydroxy(lower)alkyl ester such as hydroxyethyl ester; lower alkoxy(lower)alkyl esters such as methoxymethyl ester and 1-methoxyethyl ester; and optionally substituted aryl esters such as, for example, phenyl ester, tolyl ester, t-butylphenyl ester, salicyl ester, 3,4-di-methoxyphenyl ester and benzamidophenyl ester; and aryl(lower)alkyl ester such as benzyl ester, trityl ester and benzhydryl ester.

The amide of A mean a group represented by the formula —CONR'R", wherein each of R' and R" is hydrogen, lower alkyl, aryl, alkyl- or aryl-sulfonyl, lower alkenyl and lower alkynyl, and include for example lower alkyl amides such as methylamide, ethylamide, dimethylamide and diethylamide; arylamides such as anilide and toluidide; and alkyl- or aryl-sulfonylamides such as methylsulfonylamide, ethylsulfonylamide and tolylsulfonylamide.

Preferred examples of L and M include hydroxy and oxo, and especially, M is hydroxy and L is oxo which has a 5-membered ring structure of, so called, PGE type.

Preferred example of A is —COOH, its pharmaceutically acceptable salt, ester or amide thereof.

Preferred example of $X_1$ and $X_2$ is fluorine, so called, for example, 16,16-difluoro type.

Preferred $R_1$ is a hydrocarbon residue containing 1-10 carbon atoms, preferably 6-10 carbon atoms. Further, at least one carbon atom in the aliphatic hydrocarbon is optionally substituted by oxygen, nitrogen or sulfur. Examples of $R_1$ include, for example, the following groups:
—$CH_2$—$CH_2$—$CH_2$—$CH_2$—$CH_2$—$CH_2$—,
—$CH_2$—CH=CH—$CH_2$—$CH_2$—$CH_2$—,
—$CH_2$—$CH_2$—$CH_2$—$CH_2$—CH=CH—,
—$CH_2$—C≡C—$CH_2$—$CH_2$—$CH_2$—,
—$CH_2$—$CH_2$—$CH_2$—$CH_2$—O—$CH_2$—,
—$CH_2$—CH=CH—$CH_2$—O—$CH_2$—,
—$CH_2$—C≡C—$CH_2$—O—$CH_2$—,
—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—,
—$CH_2$—$CH_2$—$CH_2$—$CH_2$—$CH_2$—CH=CH—,
—$CH_2$—C≡C—$CH_2$—$CH_2$—$CH_2$—$CH_2$—,
—$CH_2$—$CH_2$—$CH_2$—$CH_2$—$CH_2$—CH($CH_3$)—$CH_2$—,
—$CH_2$—$CH_2$—$CH_2$—$CH_2$—CH($CH_3$)—$CH_2$—,
—$CH_2$—$CH_2$—$CH_2$—$CH_2$—$CH_2$—$CH_2$—$CH_2$—$CH_2$—,
—$CH_2$—CH=CH—$CH_2$—$CH_2$—$CH_2$—$CH_2$—$CH_2$—,
—$CH_2$—$CH_2$—$CH_2$—$CH_2$—$CH_2$—$CH_2$—CH=CH—,
—$CH_2$—C≡C—$CH_2$—$CH_2$—$CH_2$—$CH_2$—$CH_2$—, and
—$CH_2$—$CH_2$—$CH_2$—$CH_2$—$CH_2$—$CH_2$—CH($CH_3$)—$CH_2$—.

Preferred Ra is a hydrocarbon containing 1-10 carbon atoms, more preferably, 1-8 carbon atoms. Ra may have one or two side chains having one carbon atom.

The configuration of the ring and the α- and/or ω chains in the above formula (I) and (II) may be the same as or different from that of the primary PGs. However, the present invention also includes a mixture of a compound having a primary type configuration and a compound of a non-primary type configuration.

In the present invention, the PG compound which is dihydro between 13 and 14, and keto(=O) at 15 position may be in the keto-hemiacetal equilibrium by formation of a hemiacetal between hydroxy at position 11 and keto at position 15.

For example, it has been revealed that when both of $X_1$ and $X_2$ are halogen atoms, especially, fluorine atoms, the compound contains a tautomeric isomer, bicyclic compound.

If such tautomeric isomers as above are present, the proportion of both tautomeric isomers varies with the structure of the rest of the molecule or the kind of the substituent present. Sometimes one isomer may predominantly be present in comparison with the other. However, it is to be appreciated that the present invention includes both isomers.

Further, the 15-keto-PG compounds used in the invention include the bicyclic compound and analogs or derivatives thereof.

The bicyclic compound is represented by the formula (III)

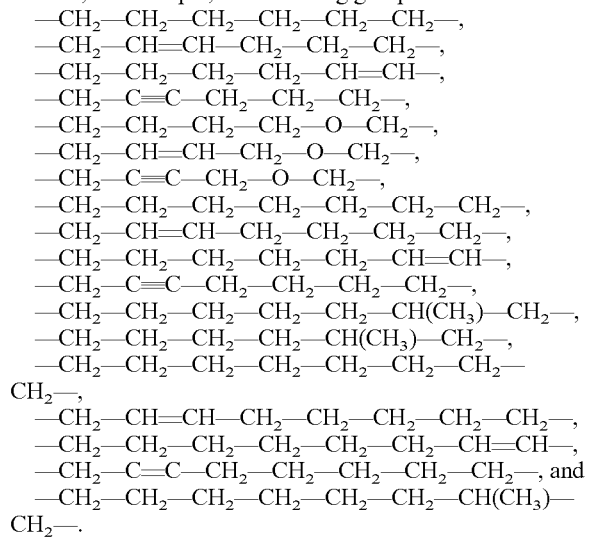

wherein, A is —$CH_3$, or —$CH_2OH$, —$COCH_2OH$, —COOH or a functional derivative thereof;
$X_1'$ and $X_2'$ are hydrogen, lower alkyl, or halogen;
Y is

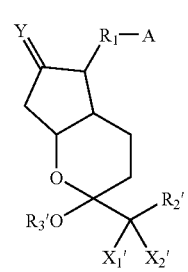

wherein $R_4'$ and $R_5'$ are hydrogen, hydroxy, halogen, lower alkyl, lower alkoxy or hydroxy(lower)alkyl, wherein $R_4'$ and $R_5'$ are not hydroxy and lower alkoxy at the same time.

$R_1$ is a saturated or unsaturated divalent lower or medium aliphatic hydrocarbon residue, which is unsubstituted or substituted with halogen, alkyl, hydroxy, oxo, aryl or heterocyclic group, and at least one of carbon atom in the aliphatic hydrocarbon is optionally substituted by oxygen, nitrogen or sulfur; and $R_2'$ is a saturated or unsaturated lower or medium aliphatic hydrocarbon residue, which is unsubstituted or substituted with halogen, oxo, hydroxy, lower alkoxy, lower alkanoyloxy, cyclo(lower)alkyl, cyclo(lower)alkyloxy, aryl, aryloxy, heterocyclic group or hetrocyclic-oxy group; lower alkoxy; lower alkanoyloxy; cyclo(lower)alkyl; cyclo(lower)alkyloxy; aryl; aryloxy; heterocyclic group; heterocyclic-oxy group.

$R_3^1$ is hydrogen, lower alkyl, cyclo(lower)alkyl, aryl or heterocyclic group.

Furthermore, while the compounds used in the invention may be represented by a formula or name based on keto-type regardless of the presence or absence of the isomers, it is to be noted that such structure or name does not intend to exclude the hemiacetal type compound.

In the present invention, any of isomers such as the individual tautomeric isomers, the mixture thereof, or optical isomers, the mixture thereof, a racemic mixture, and other steric isomers may be used in the same purpose.

Some of the compounds used in the present invention may be prepared by the method disclosed in U.S. Pat. Nos. 5,073,569, 5,166,174, 5,221,763, 5,212,324, 5,739,161 and 6,242,485 these cited references are herein incorporated by reference).

According to the present invention a mammalian subject may be treated by the instant invention by administering the compound used in the present invention. The subject may be any mammalian subject including a human. The compound may be applied systemically or topically. Usually, the compound may be administered by oral administration, intravenous injection (including infusion), subcutaneous injection, intra rectal administration, intra vaginal administration, transdermal administration and the like. The dose may vary depending on the strain of the animal, age, body weight, symptom to be treated, desired therapeutic effect, administration route, term of treatment and the like. A satisfactory effect can be obtained by systemic administration 1-4 times per day or continuous administration at the amount of 0.001-1000 µg/kg per day, more preferably 0.01-100 µg/kg, most preferably 0.1-10 µg/kg.

The compound may preferably be formulated in a pharmaceutical composition suitable for administration in a conventional manner. The composition may be those suitable for oral administration, injection or perfusion as well as it may be an external agent, suppository or pessary.

The composition of the present invention may further contain physiologically acceptable additives. Said additives may include the ingredients used with the prostaglandin compound such as excipient, diluent, filler, resolvent, lubricant, adjuvant, binder, disintegrator, coating agent, cupsulating agent, ointment base, suppository base, aerozoling agent, emulsifier, dispersing agent, suspending agent, thickener, tonicity agent, buffering agent, soothing agent, preservative, antioxidant, corrigent, flavor, colorant, a functional material such as cyclodextrin and biodegradable polymer, stabilizer. The additives are well known to the art and may be selected from those described in general reference books of pharmaceutics.

The amount of the above-defined compound in the composition of the invention may vary depending on the formulation of the composition, and may generally be 0.00001-10.0 wt %, more preferably 0.0001-1.0 wt %, most preferably 0.001-0.1%.

Examples of solid compositions for oral administration include tablets, troches, sublingual tablets, capsules, pills, powders, granules and the like. The solid composition may be prepared by mixing one or more active ingredients with at least one inactive diluent. The composition may further contain additives other than the inactive diluents, for example, a lubricant, a disintegrator and a stabilizer. Tablets and pills may be coated with an enteric or gastroenteric film, if necessary. They may be covered with two or more layers. They may also be adsorbed to a sustained release material, or microcapsulated. Additionally, the compositions may be capsulated by means of an easily degradable material such gelatin. They may be further dissolved in an appropriate solvent such as fatty acid or its mono, di or triglyceride to be a soft capsule. Sublingual tablet may be used in need of fast-acting property.

Examples of liquid compositions for oral administration include emulsions, solutions, suspensions, syrups and elixirs and the like. Said composition may further contain a conventionally used inactive diluents e.g. purified water or ethyl alcohol. The composition may contain additives other than the inactive diluents such as adjuvant e.g. wetting agents and suspending agents, sweeteners, flavors, fragrance and preservatives.

The composition of the present invention may be in the form of spraying composition, which contains one or more active ingredients and may be prepared according to a known method.

Examples of the injectable compositions of the present invention for parenteral administration include sterile aqueous or non-aqueous solutions, suspensions and emulsions. Diluents for the aqueous solution or suspension may include, for example, distilled water for injection, physiological saline and Ringer's solution.

Non-aqueous diluents for solution and suspension may include, for example, propylene glycol, polyethylene glycol, vegetable oils such as olive oil, alcohols such as ethanol and polysorbate. The composition may further comprise additives such as preservatives, wetting agents, emulsifying agents, dispersing agents and the like. They may be sterilized by filtration through, e.g. a bacteria-retaining filter, compounding with a sterilizer, or by means of gas or radioisotope irradiation sterilization. The injectable composition may also be provided as a sterilized powder composition to be dissolved in a sterilized solvent for injection before use.

The present external agent includes all the external preparations used in the fields of dermatology and otolaryngology, which includes ointment, cream, lotion and spray.

Another form of the present invention is suppository or pessary, which may be prepared by mixing active ingredients into a conventional base such as cacao butter that softens at body temperature, and nonionic surfactants having suitable softening temperatures may be used to improve absorbability.

The term "treatment" used herein includes any means of control such as prevention, care, relief of the condition, attenuation of the condition and arrest of progression.

The pharmaceutical composition of the present invention may further contain other pharmacological ingredients as far as they do not contradict the purpose of the present invention.

The further details of the present invention will follow with reference to test examples, which, however, are not intended to limit the present invention.

EXAMPLE 13,14-dihydro-15-keto-16,16-difluoro-$PGE_1$ was used as the test substance. Test capsule for oral administration containing 24 µg of the test substance and placebo capsule made from inert ingredients which was identical to the test capsule were prepared.

Volunteers were divided into 4 groups. The test groups received 24, 48 and 72 µg of the test substance per day respectively and the control group received the placebo. All volunteers were instructed to take one capsule before each meal (morning-, day- and evening-time) everyday for 21 days. Test group I (27 volunteers) received 24 µg of the test substance per day by taking the test capsule at the morning time and the placebo capsule at each of the day and evening times; test group II (32 volunteers) received 48 µg of the test substance per day by taking the test capsule at each of the morning and evening times and the placebo capsule at the day time; test group III (32 volunteers) received 72 µg of the test substance by taking the test capsule three times per day. Control group (33 volunteers) received the placebo capsule every time. Volunteers were instructed to take each capsule with 8 ounces of water prior to eating a meal. Body weight was measured before and 3 weeks after the initiation of the administration.

FIG. 1 shows the changes of body weight from the pre-values in each group at 3 weeks after the initiation of the administration. As shown in FIG. 1, body weight reductions were observed in all test groups while an increase was observed in the control group. The body weight of the test groups decreased in a dose dependent manner.

The invention claimed is:

1. A method for treating obesity in a mammalian subject, which comprises administering to a mammalian subject in need of reduction of body weight an effective amount of a compound as shown by the following Formula (II) to reduce body weight:

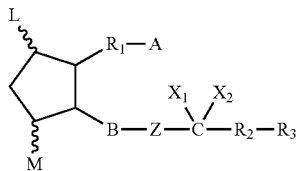

(II)

wherein L is oxo and M is hydrogen or hydroxy;
A is —COOH or a salt, ester or amide thereof;
B is —CH$_2$—CH$_2$—;
Z is

$X_1$ and $X_2$ are halogen;
$R_1$ is a saturated or unsaturated bivalent lower or medium aliphatic hydrocarbon residue;
$R_2$ is a single bond or lower alkylene; and
$R_3$ is lower alkyl;
wherein said treating comprises care, relief, attenuation, or arrest of progression of obesity.

2. The method as described in claim 1, wherein $X_1$ and $X_2$ are fluorine.

3. The method as described in claim 1, wherein $X_1$ and $X_2$ are fluorine, $R_2$ is single bond and $R_3$ is —CH$_2$—CH$_2$—CH$_2$—CH$_3$ or —CH$_2$—CH(CH$_3$)—CH$_2$—CH$_3$.

4. The method as described in claim 1, which comprises systemic administration 1-4 times per day or continuous administration at the amount of 0.01-100 μg/kg per day.

5. The method as described in claim 4, wherein the administration is at the amount of 0.1-10 μg/kg per day.

6. A method for reducing body weight in a mammalian subject which comprises administering to a mammalian subject in need of treatment for obesity an effective amount of a compound as shown by the following Formula (II):

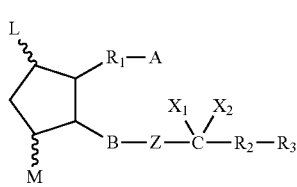

(II)

wherein L is oxo and M is hydrogen or hydroxy;
A is —COOH or a salt, ester or amide thereof;
B is —CH$_2$—CH$_2$—;
Z is

$X_1$ and $X_2$ are halogen;
$R_1$ is a saturated or unsaturated bivalent lower or medium aliphatic hydrocarbon residue;
$R_2$ is a single bond or lower alkylene; and
$R_3$ is lower alkyl;
wherein said treating comprises care, relief, attenuation, or arrest of progression of obesity.

7. A method for treating obesity in a mammalian subject, which comprises administering to a mammalian subject in need of reduction of body weight an effective amount of a compound which is 13,14-dihydro-15-keto-16,16-difluoro PGE$_1$ or a salt, ester or amide thereof or 13,14-dihydro-15-keto-16,16-difluoro-18-methyl PGE$_1$ or a salt, ester or amide thereof to reduce body weight, wherein said treating comprises care, relief, attenuation, or arrest of progression of obesity.

8. A method for treating obesity in a mammalian subject, which comprises administering to a mammalian subject in need of reduction of body weight an effective amount of 13,14-dihydro-15-keto-16,16-difluoro PGE$_1$ to reduce body weight, wherein said treating comprises care, relief, attenuation or arrest of progression of obesity.

9. A method for reducing body weight in a mammalian subject, which comprises administering to a mammalian subject in need of treatment for obesity an effective amount of 13,14-dihydro-15-keto-16,16-difluoro PGE$_1$, wherein said treating comprises care, relief, attenuation or arrest of progression of obesity.

10. A method for treating obesity in a mammalian subject, which comprises administering to a mammalian subject in need of reduction of body weight an effective amount of 13,14-dihydro-15-keto-16,16-difluoro-18-methyl PGE$_1$ to reduce body weight, wherein said treating comprises care, relief, attenuation or arrest of progression of obesity.

11. A method for reducing body weight in a mammalian subject, which comprises administering to a mammalian subject in need of treatment for obesity an effective amount of 13,14-dihydro-15-keto-16,16-difluoro-18-methyl PGE$_1$, wherein said treating comprises care, relief, attenuation or arrest of progression of obesity.

12. A method for reducing body weight in a mammalian subject which comprises administering to a mammalian subject in need of treatment for obesity an effective amount of 13,14-dihydro-15-keto-16,16-difluoro PGE$_1$ or a salt, ester or amide thereof or 13,14-dihydro-15-keto-16,16-difluoro-18-methyl PGE$_1$ or a salt, ester or amide thereof, wherein said treating comprises care, relief, attenuation or arrest of progression of obesity.

* * * * *